United States Patent [19]

Bliznakov

[11] 4,156,718

[45] May 29, 1979

[54] CONTROL AND REVERSAL OF THE IMMUNOLOGICAL SENESCENCE

[75] Inventor: Emile G. Bliznakov, Ridgefield, Conn.

[73] Assignee: The New England Institute, Inc., Ridgefield, Conn.

[21] Appl. No.: 859,959

[22] Filed: Dec. 12, 1977

Related U.S. Application Data

[63] Continuation of Ser. No. 743,411, Nov. 19, 1976, abandoned.

[51] Int. Cl.$^2$ ..................... A61K 37/48; A61K 31/12
[52] U.S. Cl. ...................................... 424/94; 424/331
[58] Field of Search .................................. 424/94, 331

[56] References Cited

PUBLICATIONS

Bliznakov–Proc. Internat. Sym. Coenzyme Q–Hakone, Japan, 1976.
Bliznakov et al.–Separatum Experientia, vol. 26 (1970) pp. 953–954.
Heller–Perspectives in Biol. & Med., vol. 16, No. 2, pp. 181–187.

*Primary Examiner*—Sam Rosen
*Attorney, Agent, or Firm*—Pennie & Edmonds

[57] ABSTRACT

The invention relates to a method of controlling and/or reversing the immunological senescence in animals and humans by administering thereto coenzymes $Q_4$ to at least $Q_{13}$ and particularly coenzyme $Q_{10}$.

4 Claims, 2 Drawing Figures

CONTROL AND REVERSAL OF THE IMMUNOLOGICAL SENESCENCE

This is a continuation of application Ser. No. 743,411 filed Nov. 19, 1976, now abandoned.

BACKGROUND OF THE INVENTION

The human body is a tremendous complex of chemical, biochemical and physiological processes all being carried on simultaneously. The incredibly complex control of these thousands of chemical and physiological processes is coded into the DNA and RNA of the genes. It is postulated that as people became older and the RNA and DNA and their messages became increasingly "blurred" with time, the control of this enormous complex would begin to lose its ability, among other things, to repair wear and tear.

The body is subject to huge numbers of destructive forces including physical, chemical and biological insults. Among the noxious physical insults is ionizing radiation from many different sources that are completely unavoidable in everyday life. Chemical insults are derived not only from synthetic but from many natural chemicals that are noxious and to which we are exposed. Biological insults are in the form of organisms such as viruses, bacteria and fungi and many of their wastes and noxious products. There is, in sum, a literal barrage of insults which make up our daily environment. It is the repair mechanism which must circumvent these destructive forces. Clearly, if the coded DNA information which controls the repair processes becomes damaged, the stigmata of age will begin.

If you look at the aging process in the last several decades of human life, you can see the repair process is increasingly impaired. Elastic tissue cannot be repaired and wrinkles occur. Muscles and joints can no longer take the punishment of youth. Cancer and other disease-producing agents which are omni-present can no longer be easily rejected. Thus, the body becomes more susceptible to infections, malignant tumors, and a host of other effects of age which, in youth, was of no concern because the body could cope with such everyday challenges.

Coenzyme Q is now generally recognized as an important component of the mitochondrial electron transport processes of respiration and coupled oxidative phosphorylation, and therefore is of fundamental importance to the intracellular energy-producing systems. Evidence has been obtained for the existence of coenzyme Q deficiencies in some pathological processes in: human cardiac, gingival and dystrophic tissues, rats with induced hypertension, mice with hereditary muscular dystrophy, Friend virus induced leukemia and others. The therapeutic application and potential of coenzyme Q was reviewed by Folkers in Iternat. J. Vit. Res. 39:334 (1969) and Cancer Chemoth. Rep. 4:19 (1974).

Coenzyme Q is now among the agents being used experimentally and clinically to enhance nonspecifically the host resistance. In contrast to other materials in use for this purpose, extensive toxicological studies, including those of the New England Institute, revealed no significant abnormalities that would contraindicate the use of coenzyme Q in humans.

Administration of various members of the coenzyme Q family into experimental animals results in increased resistance to a variety of bacterial and protozoal infections, as well as viral and chemical carcinogeneses. It has been postulated that this enhanced resistance is mediated via stimulation of various parameters of the host defense system, a process which has high cellular energy requirement.

BRIEF SUMMARY OF THE INVENTION

The invention involves the adminstration to a host, man or lower animals, of coenzymes $Q_4$ to at least $Q_{13}$, particularly $Q_{10}$, in a sufficient amount to control, e.g., stabilize and/or reverse the immunological senescence or aging in the particular host being treated.

It has been found that host defense system is subject to age-related changes occurring in both animals and man, although it is only in laboratory animals that the phenomenon has been well studied. These age-related changes are characterized in general as a gradual decline of the activity of many parameters of the host defense system. This decline forms the base for a definitive relationship between senescence and an increased rate of incidence and mortality due to infectious diseases and cancer in animals and man.

The present invention utilizes the decline of the humoral immunological responsiveness in aged mice as a representative parameter of the host defense system and the compensation and restoration of this decline by administration of coenzyme $Q_{10}$.

DETAILED DESCRIPTION OF THE INVENTION

The coenzymes Q used according to this invention are well known and have the formula

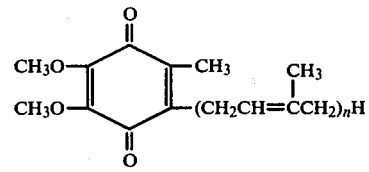

where n is 4 to at least 13.

The coenzymes are generally commercially available or can be readily made by known processes.

The term "$Q_4$ to at least $Q_{13}$" is used to describe the coenzymes according to the invention and is based on present knowledge. Experiments to date show little activity for the coenzymes lower than $Q_4$. Coenzymes higher than $Q_{13}$ have not been available for testing and therefore no useful upper limit can be mentioned at this time. It can be scientifically assumed, however, that coenzymes above $Q_{13}$ would be useful, $Q_{14}$ and $Q_{15}$ for example, and that there will be some upper limit where the activity of the coenzymes will begin to fall off. When these higher coenzymes are available for testing, it would be a simple matter for one skilled in the art to test them for activity, for example, as shown in the detailed description of the invention below. $Q_{10}$ has been noted as being most advantageous and this is particularly so in human use since $Q_{10}$ predominate in the cells of the human body. With regard to other animals, other coenzymes Q might be more advantageous. For example, in animals where $Q_9$ or $Q_8$ predominate, $Q_9$ or $Q_8$ might be more effective than $Q_{10}$. The term $Q_4$ to at least $Q_{13}$ thus includes those coenzymes above $Q_{13}$ which are capable and operative to control and/or reverse the immunological senescence in animals and humans.

The coenzymes can be administered in conventional and well known manner, such as by injection or orally. Injection is more convenient with the lower animals, but oral administration is preferred with humans. The optimum amount in mice is 125 μg, as can be seen from FIG. 2. In humans and other animals the optimum dosage can be readily determined by similar routine experimentation. The amount should obviously be sufficient to accomplish the purposes of this invention, e.g., to reverse the depression of the host defense resistance which has been depressed or weakened due to aging. Coenzymes Q, particularly $Q_{10}$, are extremely non-toxic and very high doses can be tolerated without toxic effect. Generally the dose for humans would be between about 300 to 500 mg. per week. As with many other drugs or medicines such as cortisone, the dosage level and dosage protocol can be determined by laboratory testing and/or clinical response for each individual patient.

EXAMPLE

Materials and Methods

Female CFI young adult (10 weeks old) and aged (22 months old) mice were used throughout the experiment. They were purchased from Charles River Breeding Laboratories, Inc., Wilmington, Md. (Carworth Division) and were maintained in airconditioned room (22°±1° C.) on a 12-hour light and dark cycle in metal cages with free access to food and water.

Fresh sterile sheep red blood cells (SRBC, Baltimore Biological Laboratories, Baltimore, Md.) were centrifuged and washed three times with sterile 0.9% sodium chloride solution (saline). Primary immunization was accomplished with a dose of $5.7 \times 10^7$ SRBC per mouse, suspended in 0.2 ml saline, and administered via the tail vein. The day of the antigen administration is designated as day 0.

Commercially available, substantially pure, coenzyme $Q_{10}$ (2,3-dimethoxy-5-methyl-6-decaprenyl benzoquinone) was used and was administered as an emulsion in sterile 5% glucose solution containing 0.4% of Tween 20 (polyoxyethylene sorbitol monolaurate) used as emulsifier. The concentration of coenzyme $Q_{10}$ in the emulsion was 250 μg/ml. The emulsion (total volume 200 ml) was prepared in a 500 ml Waring blender, kept in a water bath at 60° C. and protected from light. The time of homogenization was 45 seconds. The particle size of the emulsion was under 5 μm. The method used to prepare the emulsion and the subsequent handling are of critical importance.

On day four after the SRBC administration, and 4 h before the first blood collection, six groups of 22 months old mice (25 mice in each group) were treated with six different doses of coenzyme $Q_{10}$ emulsion injected into the tail vein, namely 25, 50, 75, 100, 125 and 150 μg/mouse.

The control mice (50 mice, 22 months old and 50 mice, 10 weeks old) were injected with the same mixture, omitting coenzyme $Q_{10}$.

At suitable intervals as shown in FIG. 1 after the administration of coenzyme $Q_{10}$, blood was collected from each mouse with heparinized capillary tubes by retroorbital venus plexus puncture. Equal volumes of blood from all animals in a group were pooled, the plasma was separated by centrifugation and the samples were stored at −40° C. until hemolysin titers were determined. This determination was carried out using the 50% end point method. (Experimental Immunochemistry, 2nd Edition, C.C. Thomas—publisher 1961). Eight to ten plasma dilutions were used. The best fitting regression line between probit percent hemolysis and the log of the plasma dilution was determined by computer analysis. The experimental points shown on the figures represent the determined values, with standard deviation indicated.

Control mice (25 mice, 22 months old, and 25 mice, 10 weeks old) were sacrificed, weighed and organs (spleen, liver and thymus) were excised and weighed. The data obtained were statistically analyzed by the student's t-test.

All glassware was heated for 5 hr. at 170° C. Nonpyrogenic sterile saline and sterile glucose solutions (Travenol Laboratories, Deerfield, Illinois), syringes, needles and pipets were used throughout.

Possible contamination with bacterial endotoxin (a strong toxic stimulant of the host defense system activity) of the components used for preparation of emulsions was precluded by the exclusive use of only nonpyrogenic materials. Criteria recommended by the U.S. Pharmacopeia were used for evaluation.

Figure 1:
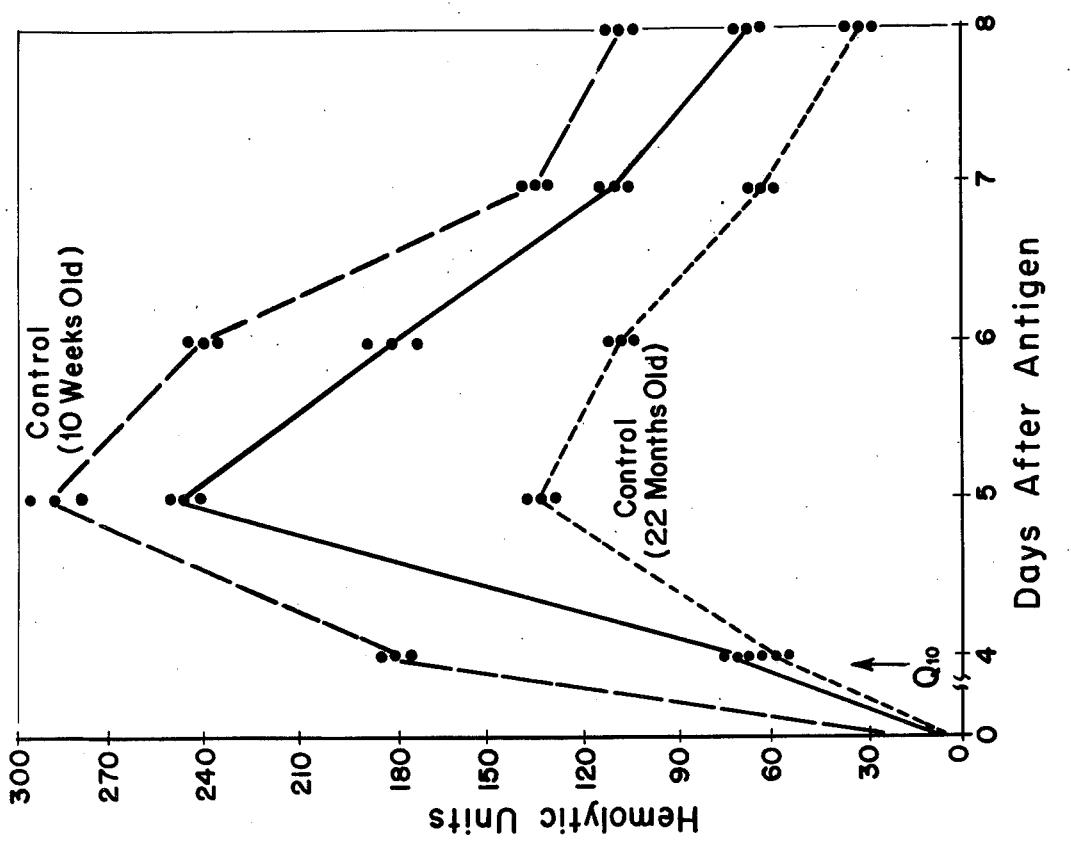
FIG. 1 shows the hemolytic primary immune response in 10 weeks and 22 months old CFI female mice, and compensation of the age dependent supression of this response by intravenous administration of coenzyme $Q_{10}$ emulsion (125 μg/mouse). The experimental points shown represent the determined values on pooled plasma from 25 mice with standard deviations indicated.

The results of the experiment showed marked suppression of the humoral hemolytic, primary immune response as a function of age of the mice and is demonstrated in FIG. 1. Clearly, the hemolytic antibody level in 22 months old mice is less than 50% of the level obtained in 10 weeks old mice, and this is not accompanied by any shifting of the appearance of the peak antibody level day.

The profound hemolytic antibody depression in old mice can be partially reversed by a single intravenous administration of coenzyme $Q_{10}$ on day 4 (FIG. 1).

Figure 2:
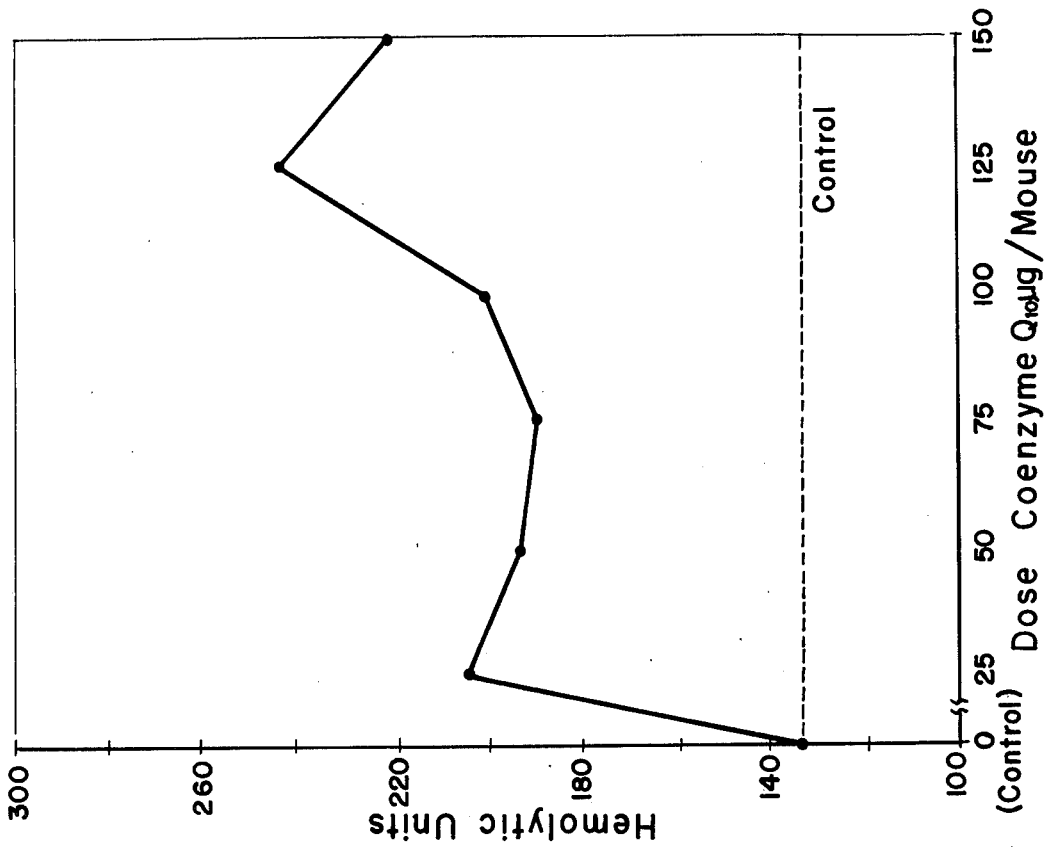
FIG. 2 shows the compensation of the suppressed hemolytic primary immune response in 22 months old mice on the peak antibody day (day 5 after the antigen administration) as a function of the dose of coenzyme $Q_{10}$. The experimental points shown represent the determined values on pooled plasma from 25 mice with standard deviations indicated.

FIG. 2 illustrates the dose (coenzyme $Q_{10}$)—response (hemolytic antibody level on day 5) relationship in 22 months old mice.

The organs' weight data and the ratio between liver, spleen and thymus weight and body weight are presented in Table 1. The results show that the body, liver and spleen weight continue to increase with age, but the ratio between the liver and the spleen and the body weight remains practically constant. In contrast, the thymus weight continues to increase with age, but this increase is at a much slower rate than the body weight increase which results in a significantly lower value of the thymus weight/body weight ratio. This ratio in 22 months old mice represents only 69.6% of the same ratio in 10 weeks old mice.

Although bone marrow (B) lymphocytes are directly involved in antibody formation, it is now a well recognized postulate that their collaboration with thymus derived (T) lymphocytes is necessary for the development of a normal humoral immunological response to certain antigens. This resulted in the concept of two distinct groups of antigens, thymus-dependent and thymus-independent, or as some prefer to designate them, antigens that can activate T cells and those which cannot. For some antigens the interaction of T cells—B cells is initiated by accessory cells (A cells, macrophages) which act by processing the antigen or by supplying necessary extracellular factor(s).

Systemic investigations on deficiencies of immunocompetent cells of aged mice indicate that both B cells and T cells mediated-immune responses decline with advancing age. In contrast, macrophage populations from young and old mice are indistinguishable. This implies that the afferent compartment of the immune system is not engaged in the immunological impairment manifested in old mice.

Furthermore, a 10-fold reduction in the proliferative capacity of T cells and a 5- to 10-fold reduction in B cell proliferative capacity in old mice has been reported. As a result, the T - B cell ratio is altered. Their studies revealed also that an optimal ratio of T - B cells is required to generate a maximal response to SRBC and that the optimal ratio is the same for both young and old cells.

In a more recent study it has been observed that in humans absolute and percentage B cell counts showed no significant and gradual depression with advancing age. Although B cell numbers remain stable, B cell functions were impaired with aging.

Surprisingly, there have been few reports on age-related changes in the functional capacity of the thymus. It has been shown that the extent to which T cells can mature is dependent upon the degree of involution the thymic tissue has undergone with age. It was suggested that the thymus dependent T cells are the key system whose exhaustion is responsible for aging in mammals and probably other vertebrates and that with aging the thymus begins producing not only fewer cells, but also less efficient T cells. More recently it has emphasized that physiologic thymic function(s) must continue throughout life in order to maintain T cell functions.

The results of this invention clearly demonstrate the profound suppression of the primary immune response in aged mice to SRBC, a thymus-dependent antigen. This suppression is accompanied by a lower value of thymus weight/body weight ratio. In contrast, the ratio spleen weight/body weight and liver weight/body weight in 10 weeks and in 22 months old mice remains almost constant. A single administration of coenzyme $Q_{10}$ emulsion, a stimulant of the host defense system, partially but significantly compensates the age-dependent suppression of the humoral immune response. This compensation is dependent on the dose of coenzyme $Q_{10}$. The nonlinear response of the host defense system upon stimulation has been extensively studied. This response forms a W- and M-shaped curve (depending on the selection of parameters used for the representation) and is the property of the host defense system and not of the stimulant used.

Indirect evidence suggest that coenzyme Q stimulates both the B cell and T cell mediated responses. Furthermore, administration of coenzyme Q in experimental animals and humans induces no significant cellular proliferative effect on the host defense system. Thus the stimulating effect is believed to be mediated via a more efficient performance by existing cells rather than by an increased number of cells. This more efficient performance conferred by coenzyme $Q_{10}$ compensates for the decline of B cell and especially T cell dependent immunological responsiveness in aged mice and probably restores the functional balance of T - B cells required for an optimal response to SRBC. A possible effect via the afferent compartment of the immune system (macrophages) is not considered here because of the delayed administration of coenzyme $Q_{10}$ (on day 4 after the antigen).

An additional intriguing possibility is suggested by some limited studies, by others implying an impairment of the intracellular process of respiration at the mitochondrial level in senescence. This is accompanied also by changes in the mitochondrial ultrastructure. Similarly, it has been demonstrated that energy linked processes are partially or completely lost during aging of mitochondria but this is within certain limits, a reversible phenomenon. Further qualitative and quantitative studies at this mitochondrial level should shed light on the relationship between immunological impairment and the resulting increased incidence of cancer and infections in senescence as well as the compensation of this impairment by coenzyme Q.

The data set forth here show a pronounced suppression of the humoral hemolytic primary immune response in 22 months old mice as compared with this response in 10 weeks old mice. The suppression is associated with a lower value of thymus weight/body weight ratio. In contrast, the ratio spleen weight/body weight and liver weight/body weight in 10 weeks and 22 months old mice remain almost constant.

A single administration of coenzyme $Q_{10}$, a nontoxic, nonspecific stimulant of the host defense system, partially compensates the age-determined suppression of the humoral immune response.

The results are statistically significant and they are unequivocal. At the age of 22 months, there was a depression of host defense resistance in mice. This resistance was lowered by a very significant factor; more than 50%. One injection of coenzyme $Q_{10}$ restored 90% of the depressed resistance.

I claim:

1. The method of reversing the immunological senescence in aged humans and lower animals which comprises internally administering thereto a sufficient Table I BODY, LIVER, SPLEEN AND THYMUS WEIGHT IN 10 WEEKS AND 22 MONTHS OLD CF1 FEMALE MICE

| MICE AGE | MEAN BODY WT gm | % | MEAN LIVER WT mg | % | MEAN SPLEEN WT mg | % | MEAN THYMUS WT mg | % | LIVER WT mg / BODY WT gm Ratio | % | SPLEEN WT mg / BODY WT gm Ratio | % | THYMUS WT mg / BODY WT gm Ratio | % |
|---|---|---|---|---|---|---|---|---|---|---|---|---|---|---|
| 10 Weeks | 22.04 | 100.0 | 1365 | 100.0 | 90.4 | 100.0 | 40.0 | 100.0 | 62.10 | 100.0 | 4.12 | 100.0 | 1.81 | 100.0 |
| 22 Months | 37.85 | 171.7 | 2477 | 181.5 | 161 | 178.1 | 47.9 | 119.8 | 65.48 | 105.4 | 4.26 | 103.4 | 1.26 | 69.6 |

$P < 0.0001$ amount of a coenzyme $Q_4$ to at least $Q_{13}$ to reverse the depression of the host defense resistance which has been depressed or weakened due to aging.

2. The method of claim 1 in which the coenzyme is coenzyme $Q_{10}$.

3. The method of retarding or reversing the immunological senescence in aged humans or lower animals which comprises internally administering thereto a sufficient amount of a coenzyme $Q_4$ to at least $Q_{13}$ to suppress the humoral hemolytic immune response of the host which has been depressed due to aging.

4. The method of claim 3 in which the coenzyme is coenzyme $Q_{10}$.

* * * * *